United States Patent
Bischoff et al.

(10) Patent No.: US 8,632,527 B2
(45) Date of Patent: Jan. 21, 2014

(54) METHOD FOR GENERATING CONTROL DATA FOR EYE SURGERY, AND EYE-SURGICAL TREATMENT DEVICE AND METHOD

(75) Inventors: Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 369 days.

(21) Appl. No.: 12/936,380

(22) PCT Filed: Mar. 28, 2009

(86) PCT No.: PCT/EP2009/002289
§ 371 (c)(1),
(2), (4) Date: Oct. 4, 2010

(87) PCT Pub. No.: WO2009/124668
PCT Pub. Date: Oct. 15, 2009

(65) Prior Publication Data
US 2011/0034911 A1    Feb. 10, 2011

(30) Foreign Application Priority Data
Apr. 4, 2008    (DE) .................... 10 2008 017 293

(51) Int. Cl.
*A61F 9/01* (2006.01)
*A61F 9/009* (2006.01)

(52) U.S. Cl.
USPC .................................................. 606/4; 606/5

(58) Field of Classification Search
USPC ....................................................... 606/4–6
See application file for complete search history.

(56) References Cited

U.S. PATENT DOCUMENTS

| | | |
|---|---|---|
| 5,549,632 A | 8/1996 | Lai |
| 5,656,186 A | 8/1997 | Mourou et al. |
| 5,984,916 A | 11/1999 | Lai |
| 6,322,556 B1 | 11/2001 | Gwon et al. |
| 6,730,074 B2 * | 5/2004 | Bille et al. ............ 606/5 |
| 6,997,553 B2 * | 2/2006 | Tung ................. 351/159.1 |
| 2003/0220629 A1 * | 11/2003 | Bille et al. ............ 606/5 |
| 2006/0195075 A1 | 8/2006 | Muhlhoff et al. |
| 2007/0179483 A1 | 8/2007 | Muhlhoff et al. |
| 2007/0237620 A1 | 10/2007 | Muhlhoff et al. |
| 2007/0293851 A1 * | 12/2007 | Muhlhoff et al. ...... 606/11 |

(Continued)

FOREIGN PATENT DOCUMENTS

| | | |
|---|---|---|
| DE | 695 00 997 T2 | 4/1998 |
| DE | 10 2006 046 370 A1 | 4/2008 |

(Continued)

*Primary Examiner* — Sam Yao
*Assistant Examiner* — Michael M Kim
(74) *Attorney, Agent, or Firm* — Patterson Thuente Pedersen, P.A.

(57) ABSTRACT

A method for generating control data for an eye-surgical treatment device, which separates tissue layers in the eye cornea by application of a laser device, wherein a contact glass having a contact surface deforms the cornea to conform to the shape of the contact surface during the operation of the laser device. The contact surface is first placed on a cornea apex at a contact surface apex and is then pressed against the same for deforming the cornea. The method includes: generating the control data of the laser device such that the data specifies coordinates of target points located in the cornea for the laser device, and upon generation of the target point coordinates the deformation of the cornea which is present during the operation of the laser device as a result of the contact glass is taken into consideration. The invention provides that the several steps are carried out in consideration of the deformation in order to determine a displacement of a point P in the undeformed cornea caused by the deformation.

11 Claims, 7 Drawing Sheets

(56) References Cited

U.S. PATENT DOCUMENTS

2008/0078752 A1     4/2008   Bischoff et al.
2009/0281529 A1   11/2009   Carriazo

FOREIGN PATENT DOCUMENTS

| | | |
|---|---|---|
| EP | 1 159 986 A2 | 12/2001 |
| EP | 1 364 632 A1 | 11/2003 |
| EP | 1 719 483 A1 | 11/2006 |
| WO | WO 93/08677 | 5/1993 |
| WO | WO 03/002008 A1 | 1/2003 |
| WO | WO 2005/011545 A1 | 2/2005 |
| WO | WO 2005/011546 A1 | 2/2005 |
| WO | WO/2005/011547 * | 2/2005 ............... A61F 9/01 |
| WO | WO 2005/011547 A1 | 2/2005 |
| WO | WO 2005/048895 A1 | 6/2005 |

* cited by examiner

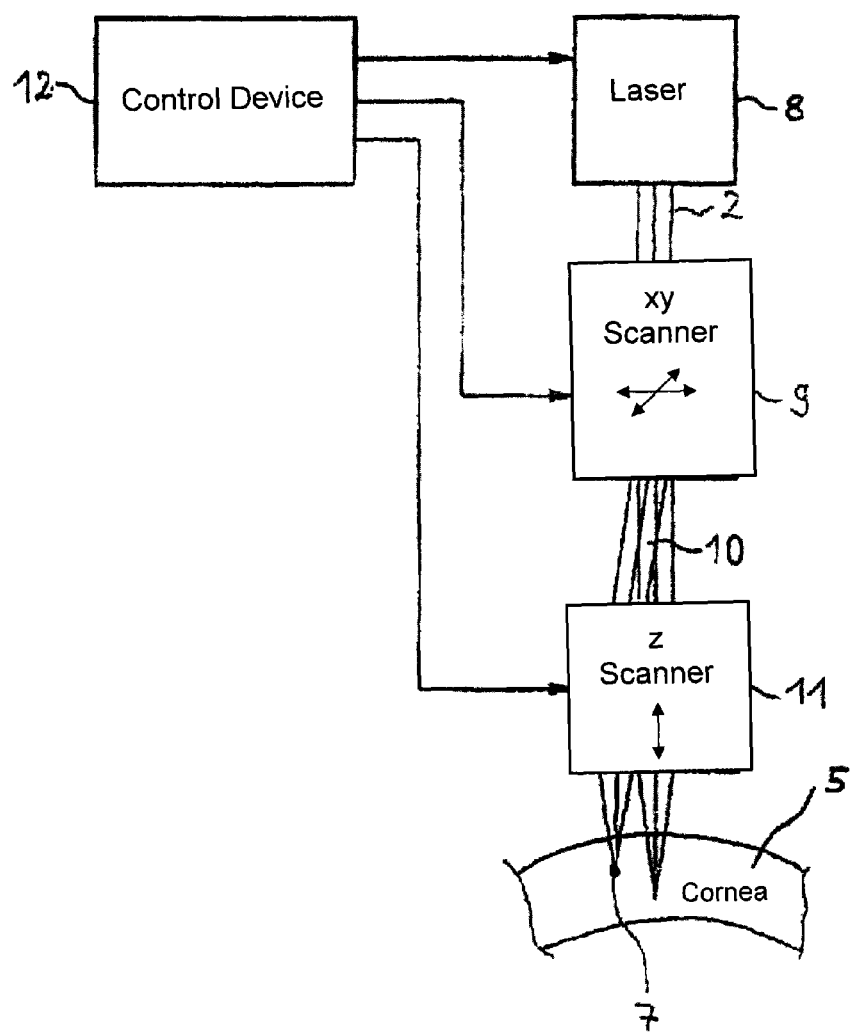

000
METHOD FOR GENERATING CONTROL DATA FOR EYE SURGERY, AND EYE-SURGICAL TREATMENT DEVICE AND METHOD

PRIORITY CLAIM

The present application is a National Phase entry of PCT Application No. PCT/EP2009/002289, filed Mar. 28, 2009, which claims priority from German Application Number 102008017293.6, filed Apr. 4, 2008, the disclosures of which are hereby incorporated by reference herein in their entirety.

BACKGROUND

The invention relates to a procedure for generating control data for an eye-surgery treatment apparatus that, by means of a laser device, separates tissue layers in the cornea of the eye, wherein, during operation of the laser device, a contact glass having a contact surface deforms the cornea into the shape of the contact surface, for which purpose the contact surface is first set, with a contact-surface vertex, onto a corneal vertex and, for the purpose of deforming the cornea, is then pressed against the latter, the procedure comprising the following steps: the control data for the laser device is generated in such a way that it specifies coordinates of target points for the laser device that are located in the cornea and, in the generation of the target-point coordinates, the deformation of the cornea, caused by the contact glass, that exists during operation of the laser device is considered.

The invention further relates to an eye-surgery treatment apparatus that comprises: a laser device for separating tissue layers of the cornea of the eye, a contact glass, which has a contact surface and which, during operation of the laser device, deforms the cornea into the shape of the contact surface, for which purpose the contact surface is first set, with a contact-surface vertex, onto a corneal vertex and, for the purpose of deforming the cornea, is then pressed against the latter, and a control device, which generates control data for the laser device in such a way that it specifies coordinates of target points for the laser device that are located in the cornea, and which, in the generation of the target-point coordinates, considers the deformation of the cornea, caused by the contact glass, that exists during the operation of the laser device.

The invention further relates to a procedure for eye-surgery treatment that, by means of a laser device, separates tissue layers in the cornea of the eye, wherein a contact glass having a contact surface is first set, with a contact-surface vertex, onto a corneal vertex and, for the purpose of deforming the cornea, is then pressed against the latter, such that the contact glass deforms the cornea into the shape of the contact surface, control data for the laser device being generated in such a way that it specifies coordinates of target points for the laser device that are located in the cornea and, in the generation of the target-point coordinates, the deformation of the cornea, caused by the contact glass, that exists during the operation of the laser device is considered.

Finally, in addition, the invention relates to a procedure for eye-surgery treatment that, by means of a laser device, separates tissue layers in the cornea of the eye, wherein, for the purpose of deformation, a contact glass having a contact surface is pressed against the cornea, such that the contact glass deforms the cornea into the shape of the contact surface, control data for the laser device being generated in such a way that it specifies coordinates of target points for the laser device that are located in the cornea and, in the generation of the target-point coordinates, the deformation of the cornea, caused by the contact glass, that exists during the operation of the laser device is considered.

For a long time, spectacles have constituted the classic way of correcting defective vision of the human eye. Now, however, increasing use is being made of refractive surgery, which corrects defective vision by altering the cornea of the eye. In such cases, the aim of all procedures of operation is purposefully to alter the cornea in order to influence the refraction of light. Differing procedures of operation are known for this purpose. Most widespread is that of so-called laser in-situ keratomileusis, also abbreviated as LASIK. In this case, a corneal lamella is first detached from the corneal surface on one side and folded to the side. This lamella can be detached by means of a mechanical microkeratome, or also by means of a so-called laser keratome, such as that distributed by, for example, Intralase Corp., Irvine, USA.

The latter produces a cut surface in the cornea through laser radiation. In this case, a plurality of processes, which are initiated by the laser radiation, take place in succession in the tissue. If the power density of the radiation is above a threshold value, an optical breakdown occurs, which produces a plasma bubble in the cornea. After the optical breakdown has occurred, the plasma bubble grows as a result of expanding gases. If the optical breakdown is not maintained, the gas produced in the plasma bubble is absorbed by the surrounding material and the bubble disappears again. Also possible are tissue-separating effects that act without a plasma bubble. For simplicity, all such processes are combined here under the term "optical breakdown", i.e. this term is intended to include, not only the optical breakdown, but also the effects in the cornea that result therefrom.

For the purpose of producing the optical breakdown, the laser radiation is applied in a pulsed manner, the pulse length being less then 1 ps. As a result, for the respective pulse, the power density required to trigger an optical breakdown is achieved only in a confined spatial region. U.S. Pat. No. 5,984,916 shows clearly in this respect that the spatial area of the optical breakdown (in this case, of the interaction produced) is highly dependent on the pulse duration. A high degree of focusing of the laser beam, in combination with the aforementioned short pulses, therefore enables the optical breakdown to be applied very precisely in the cornea.

For the purpose of producing the thin lamella, a series of optical breakdowns is then produced at predefined points by means of the laser keratome, so as to realize a cut surface that detaches the lamella from the cornea underneath the latter.

After the lamella has been detached and folded to the side, in the case of the LASIK operation there is provision for use of an excimer laser, which removes the now exposed corneal tissue through ablation. After volume located in the cornea has been vaporized in this manner, the corneal lamella is folded back again to the original place. The LASIK procedure already in use, which, insofar as a laser keratome is used, is also designated as fs-LASIK, thus exposes a cap-shaped corneal lamella, folds back the latter and ablates the exposed tissue by means of an ablation laser.

It is also mentioned in the prior art that the correction of defective vision is produced in that a lens-shaped partial volume in the corneal tissue is isolated by means of the pulsed laser radiation. Such a depiction is found, for example, in WO 2005/011545 A1. However, devices are not yet correspondingly available on the market.

The precision with which the cut surface is produced is, of course, ultimately determinative for the optical correction. This applies quite particularly to advanced laser-surgery procedures of correction of defective vision, in which a volume located in the cornea is isolated through a three-dimensional cut surface and is thus rendered removable. Unlike in the case of the laser keratome, the position of the cut surface is then directly relevant to optical correction. In the case of the conventional LASIK method, by contrast, it is exclusively the precision with which the laser ablation is performed that is important for the quality of the optical correction, which is evident even from the fact that, in a great multiplicity of operations, the production of the corneal lamella is, or has been, effected by means of a mechanical blade whose operation is comparatively imprecise.

It is further known from WO 2005/011547 A1 that a contact glass, onto which the cornea of the eye is pressed, can be used in the case of laser-surgery apparatuses. This contact glass serves to impart a fixed, defined shape to the cornea and, at the same time, to fix the eye in place. The pressing onto the contact glass thus results in a deformation of the cornea, which is considered in the determination of the coordinates of the target points in that pressing-on and deformation is considered in a coordinate transformation, which, in the WO publication, is designated as a "contact pressure transformation" and which allows for a displacement of the target points. The printed publication gives transformation equations for the case of a combination of a spherical contact glass and a spherical corneal anterior surface. Although the publication mentions that further supplements are possible by means of correction terms, it does not describe such terms. The transformation equations mentioned therein therefore apply exclusively to spherical contact glasses and spherical corneal anterior surfaces, which, however, are not always the case.

SUMMARY OF THE INVENTION

The invention is therefore based on the object of specifying an improved procedure for generating control data, an improved treatment device and an improved treatment procedure that, even beyond the boundary conditions given by WO 2005/01157 A1, are able reliably to consider the deformation of the cornea caused by the contact glass, and that therefore provide a more precise laser-surgery operation result.

This object is achieved, in one embodiment of the invention, by a procedure for generating control data for an eye-surgery treatment apparatus that, by means of a laser device, separates tissue layers in the cornea of the eye, wherein, during operation of the laser device, a contact glass having a contact surface deforms the cornea into the shape of the contact surface, for which purpose the contact surface is pressed against the cornea, the procedure comprising the following steps: the control data for the laser device is generated in such a way that it specifies coordinates of target points for the laser device that are located in the cornea and, in the generation of the target-point coordinates, the deformation of the cornea, caused by the contact glass, that exists during the operation of the laser device is considered, the following steps being executed in the consideration of the deformation, in order to determine a displacement of a point P in the non-deformed cornea, the displacement being caused by deformation:

1a) on a reference surface V of the non-deformed cornea there is determined, in relation to the point P, a point O that is located in such a way that the surface normal running through the point O goes through the point P, the reference surface being either the anterior surface itself or a surface obtained through radial contraction of the anterior surface by a bend line displacement L, 1b) a distance $\overline{SO}$ between a vertex S of the reference surface and the point O is determined, the distance $\overline{SO}$ being the arc length on the reference surface, 1c) on a contact-glass reference surface there is determined a point O' that is located at the distance $\overline{SO}$ from the contact-surface vertex, the contact-glass reference surface being either the contact surface itself or a surface obtained through radial contraction of the contact surface by the bend line displacement and/or by a thickness F' of a fluid film on the cornea, 1d) on a surface normal in the point O' there is determined a point P' that has the same distance from O' as the point P has from the point O, and 1e) the point P' is used as a point P displaced by the deformation;

and/or the following steps are executed in the consideration of the deformation, in order to determine a displacement of a point Q' in the deformed cornea, the displacement being caused by relaxation:

2a) on the contact-glass reference surface there is determined, in relation to the point Q', a point O' that is located in such a way that the surface normal running through the point O' goes through the point Q', 2b) a distance $\overline{SO'}$ between the vertex S and the point O' is determined, the distance $\overline{SO'}$ being the arc length on the contact-glass reference surface, 2c) on the reference surface there is determined a point O that is located at the distance $\overline{SO'}$ from the vertex S, 2d) on a surface normal in the point O there is determined a point Q that has the same distance from O as the point Q' has from the point O', and 2e) the point Q is used as a point Q' displaced by the relaxation.

The object is achieved, in another embodiment of the invention, by a procedure for generating control data for an eye-surgery treatment apparatus that, by means of a laser device, separates tissue layers in the cornea of the eye, wherein, during operation of the laser device, a contact glass having a contact surface deforms the cornea into the shape of the contact surface, the procedure comprising the following steps: the control data for the laser device is generated in such a way that it specifies coordinates of target points for the laser device that are located in the cornea and, in the generation of the target-point coordinates, the deformation of the cornea, caused by the contact glass, that exists during the operation of the laser device is considered, the following transformation, between a spherical coordinate system ($\phi$, $\alpha$, R), related to the non-deformed cornea, and a spherical coordinate system ($\phi'$, $\alpha'$, R') for the cornea placed against the contact glass and deformed thereby, being used:

$$\varphi = \varphi'$$
$$\alpha' \cdot R' = R \cdot \left(\alpha + \frac{c_5}{40}\alpha^5 - \frac{c_7}{84}\alpha^7 + K_1\right)$$
$$r' = R_{KGL} + r - R_{cv}\left(1 + \frac{f_4}{8}\alpha^4 - \frac{f_6}{12}\alpha^6 + K_2\right)$$

wherein $R_{KGL}$ is the radius of the contact surface, $R_{CV}$ is the radius of the non-deformed anterior surface of the cornea, $c_5$, $c_7$, $f_4$ and $f_6$ are experimentally established correction factors that can be equated approximately to 1, $K_1$ is an optional correction term for higher odd orders of $\alpha$, and $K_2$ is an optional correction term for higher odd orders of $\alpha$.

The object is achieved, in another embodiment of the invention, by a procedure for generating control data for an eye-surgery treatment apparatus that, by means of a laser device, separates tissue layers in the cornea of the eye, wherein, during operation of the laser device, a contact glass having a contact surface deforms the cornea into the shape of the contact surface, the procedure comprising the following steps: the control data for the laser device is generated in such a way that it specifies coordinates of target points for the laser device that are located in the cornea and, in the generation of the target-point coordinates, the deformation of the cornea, caused by the contact glass, that exists during the operation of the laser device is considered, the following transformation, between a spherical coordinate system ($\phi$, $\alpha$, R), related to the non-deformed cornea, and a spherical coordinate system ($\phi'$, $\alpha'$, R') for cornea that is placed against the contact glass and deformed, being used:

$$\phi = \phi'$$

$$\alpha'(R_{KGL} - F' - L) = \alpha(R_{CV} - L)$$

$$R' = R + R_{KGL} - R_{CV}$$

wherein $R_{KGL}$ is the radius of the contact surface, $R_{CV}$ is the radius of the non-deformed anterior surface of the cornea, F' is the thickness of a fluid film between the cornea and the contact surface pressed against it, and L is a displacement of a bend line of the cornea of the eye from the surface of the cornea into the interior of the cornea, which displacement has been determined experimentally, F' or L also being able to be equated approximately to zero.

The object is also achieved, in one embodiment of the invention, by a procedure for eye-surgery treatment that, by means of a laser device, separates tissue layers in the cornea of the eye, a contact glass having a contact surface being pressed with the latter against the cornea, such that the contact glass deforms the cornea into the shape of the contact surface, control data for the laser device being generated in such a way that it specifies coordinates of target points for the laser device that are located in the cornea and, in the generation of the target-point coordinates, the deformation of the cornea, caused by the contact glass, that exists during the operation of the laser device is considered, the following steps being executed in the consideration of the deformation, in order to determine a displacement of a point P in the non-deformed cornea, the displacement being caused by deformation:

1a) on a reference surface of the non-deformed cornea there is determined, in relation to the point P, a point O that is located in such a way that the surface normal running through the point O goes through the point P, the reference surface being either the anterior surface itself or a surface obtained through radial contraction of the anterior surface by a bend line displacement L, 1b) a distance $\overline{SO}$ between a vertex S of the reference surface and the point O is determined, the distance $\overline{SO}$ being the arc length on the reference surface, 1c) on a contact-glass reference surface there is determined a point O' that is located at the distance $\overline{SO}$ from the contact-surface vertex, the contact-glass reference surface being either the contact surface itself or a surface obtained through radial contraction of the contact surface by the bend line displacement and/or by a thickness F' of a fluid film on the cornea, 1d) on a surface normal in the point O' there is determined a point P' that has the same distance from O' as the point P has from the point O, and 1e) the point P' is used as a point P displaced by the deformation;

and/or the following steps are executed in the consideration of the deformation, in order to determine a displacement of a point Q' in the deformed cornea, the displacement being caused by relaxation:

2a) on the contact-glass reference surface there is determined, in relation to the point Q', a point O' that is located in such a way that the surface normal running through the point O' goes through the point Q', 2b) a distance $\overline{SO'}$ between the vertex S and the point O' is determined, the distance $\overline{SO'}$ being the arc length on the contact-glass reference surface, 2c) on the reference surface there is determined a point O that is located at the distance $\overline{SO'}$ from the vertex S, 2d) on a surface normal in the O there is determined a point Q that has the same distance from O as the point Q' has from the point O', and 2e) the point Q is used as a point Q' displaced by the relaxation.

The object is likewise achieved, in another embodiment of the invention, by means of a procedure for eye-surgery treatment that, of a laser device, separates tissue layers in the cornea of the eye, wherein, for the purpose of deformation, a contact glass having a contact surface is pressed against the cornea, such that the contact glass deforms the cornea into the shape of the contact surface, control data for the laser device being generated in such a way that it specifies coordinates of target points for the laser device that are located in the cornea and, in the generation of the target-point coordinates, the deformation of the cornea, caused by the contact glass, that exists during the operation of the laser device is considered, the following transformation, between a spherical coordinate system ($\phi$, $\alpha$, r), related to the non-deformed cornea, and a spherical coordinate system ($\phi'$, $\alpha'$, r') for cornea that is placed against the contact surface and deformed, being used:

$$\varphi = \varphi'$$

$$\alpha' \cdot R' = R \cdot \left( \alpha + \frac{c_5}{40}\alpha^5 - \frac{c_7}{84}\alpha^7 + K_1 \right)$$

$$R' = R_{KGL} + R - R_{cv}\left( 1 + \frac{f_4}{8}\alpha^4 - \frac{f_6}{12}\alpha^6 + K_2 \right)$$

wherein $R_{KGL}$ is the radius of the contact surface, $R_{CV}$ is the radius of the non-deformed anterior surface of the cornea, $c_5$, $c_7$, $f_4$ and $f_6$ are experimentally established correction factors that can be equated approximately to 1, $K_1$ is an optional correction term for higher odd orders of $\alpha$, and $K_2$ is an optional correction term for higher odd orders of $\alpha$.

Finally, the object is also achieved, in another embodiment, by a procedure for eye-surgery treatment that, by means of a laser device, separates tissue layers in the cornea of the eye, wherein, for the purpose of deformation, a contact glass having a contact surface is pressed against the cornea, such that the contact glass deforms the cornea into the shape of the contact surface, control data for the laser device being generated in such a way that it specifies coordinates of target points for the laser device that are located in the cornea and, in the generation of the target-point coordinates, the deformation of the cornea, caused by the contact glass, that exists during the operation of the laser device is considered, the following transformation, between a spherical coordinate system ($\phi$, $\alpha$, R), related to the non-deformed cornea, and a spherical coordinate system ($\phi'$, $\alpha'$, R') for cornea that is placed against the contact surface and deformed, being used:

$$\phi = \phi'$$

$$\alpha'(R_{KGL} - F' - L) = \alpha(R_{CV} - L)$$

$$R' = R + R_{KGL} - R_{CV}$$

wherein $R_{KGL}$ is the radius of the contact surface, $R_{CV}$ is the radius of the non-deformed anterior surface of the cornea, F' is the thickness of a fluid film between the cornea and the contact surface pressed against it, and L is a displacement of a bend line of the cornea of the eye from the surface of the cornea into the interior of the cornea, which displacement has been determined experimentally, F' or L also being able to be equated approximately to zero.

The object is also achieved by means of an eye-surgery treatment apparatus, which comprises: a laser device for separating tissue layers of the cornea of the eye, a contact glass, which has a contact surface and which, during operation of the laser device, deforms the cornea into the shape of the contact surface, for which purpose the contact surface is first set, with a contact-surface vertex, onto a corneal vertex and, for the purpose of deforming the cornea, is then pressed against the latter, and a control device, which generates control data for the laser device in such a way that the control data specifies coordinates of target points for the laser device that are located in the cornea, and which, in the generation of the target-point coordinates, considers the deformation of the cornea, caused by the contact glass, that exists during operation of the laser device, the control device executing the procedure according to one of the three invention variants mentioned.

Thus, the invention no longer assumes that the cornea of the eye is spherical, or that the bend line lies strictly on the surface of the cornea of the eye and that the thickness of the tear film is negligible. The approach according to the invention makes it possible to avoid differences between the intended course of the cut and that which is achieved, in particular at edge zones of the operating region. The increased precision in this case has the consequence that it is possible to work even with contact glasses, or contact surfaces, having a comparatively more pronounced curvature, whereas the prior art hitherto has tended to flatten the cornea as much as possible, despite this being disadvantageous for various reasons, in particular because of an increase in the internal pressure of the eye.

The first variant of the invention has the advantage in this case that it can also be applied in the case of a contact glass of any shape, in particular non-spherical or non-rotationally symmetrical, since each point P in the free cornea is transformed, in respect of its coordinates, to a point P' that, in the case of a deformed eye, i.e. an eye placed against the contact surface, corresponds to the point P. The procedure steps of the first variant in this case describe how, for each given point in the non-deformed cornea, the corresponding coordinates after deformation of the cornea are determined. This constitutes the so-called forward transformation. An analogous process, however, also gives rise to the back transformation for a point whose coordinates in the deformed cornea are known and whose corresponding coordinates in the non-deformed cornea, i.e. after relaxation through removal of the contact glass, are to be determined. Claim 1, and the corresponding included or parallel claims, define the forward transformation in steps 1a)-1e), and define the back transformation in steps 2a)-2e). One of the two is performed, according to the invention, in the first variant.

The procedure of the first variant has the advantage that it is generally applicable to any surface.

For the special case of a paraboloidal surface of the corneal anterior surface in combination with a spherical contact surface of the contact glass, the second variant specifies a simple approximation to coordinate transformation. For better adaptation, the correction factors used in this case can be determined from experimental data but, for simplification, they can also be equated to 1.

A further factor that can result in the actual position of the cut surface deviating from the position to be expected according to the control data is the thickness of a fluid film that, even when the cornea is in the deformed state, results in a fluid-filled gap between the corneal anterior surface and the contact surface of the contact glass. This fluid is not necessarily to be equated to a natural tear film, since, in the case of an operation, the eye is usually anaesthetized by a local anaesthetic (in drop form) and an artificial tear fluid is applied. The natural thickness of tear film is therefore not automatically present. Moreover, the thickness of fluid is additionally altered by the pressing-on and deformation. The third variant of the invention therefore considers the thickness F' of this film of fluid. A typical range for this thickness F' is 5-20 μm.

Further, optionally, it is also possible to take account of the fact that, in the deformation of the cornea, the bend line, i.e. the neutral axis of the deformation, does not run exactly on the corneal anterior surface, but can be displaced into the cornea, i.e. inwards. This displacement can be established from experimental data. In a simplified variant, it is assumed that the bend line is located on the mid-thickness of the cornea, i.e. the displacement corresponds to half the thickness of the cornea.

Further, the consideration of the fluid film thickness, or of the displacement of the bend line, can also be used for the other variants.

BRIEF DESCRIPTION OF THE DRAWINGS

The invention is explained yet more fully in the following, by way of example, with reference to the drawing, wherein:

FIG. 3 is a further schematic representation of the treatment appliance of FIG. 1.

DETAILED DESCRIPTION

Figure 1:
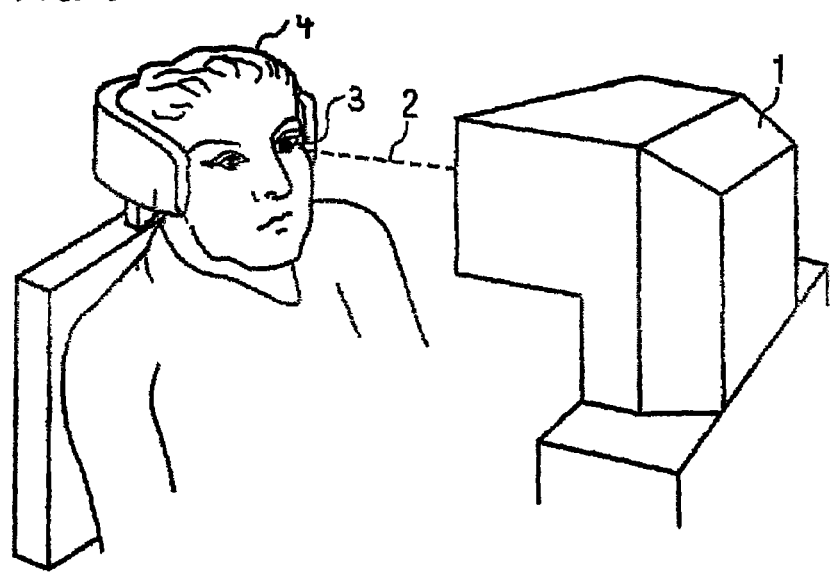
FIG. 1 is a schematic representation of a treatment apparatus, or of a treatment appliance for correction of defective vision.

FIG. 1 shows a treatment appliance 1 for an eye-surgery procedure, which is similar to that described in EP 1159986 A1, or in U.S. Pat. No. 5,549,632. By means of a treatment laser radiation 2, the treatment appliance 1 effects correction of defective vision on an eye 3 of a patient 4. The defective vision can include hyperopia, myopia, presbyopia, astigmatism, mixed astigmatism (astigmatism in which there is hyperopia in one direction and myopia in a direction at right angles thereto), aspheric errors and higher-order aberrations. In the embodiment described, the treatment laser radiation 2 is applied as a pulsed laser beam focused into the eye 3. The pulse duration in this case is, for example, in the femtosecond range, and the laser radiation 2 acts by means of non-linear optical effects in the cornea. The laser beam has, for example, 50 to 800 fs short laser pulses (preferably 100-400 fs) with a pulse repetition frequency of between 10 and 500 kHz. In the embodiment example described, the modules of the device 1 are controlled by an integrated control unit, which, however, clearly can also be realized as a stand-alone unit.

Before the treatment appliance is used, the defective vision of the eye 3 is measured by means of one or more measuring devices.

Figure 1A:
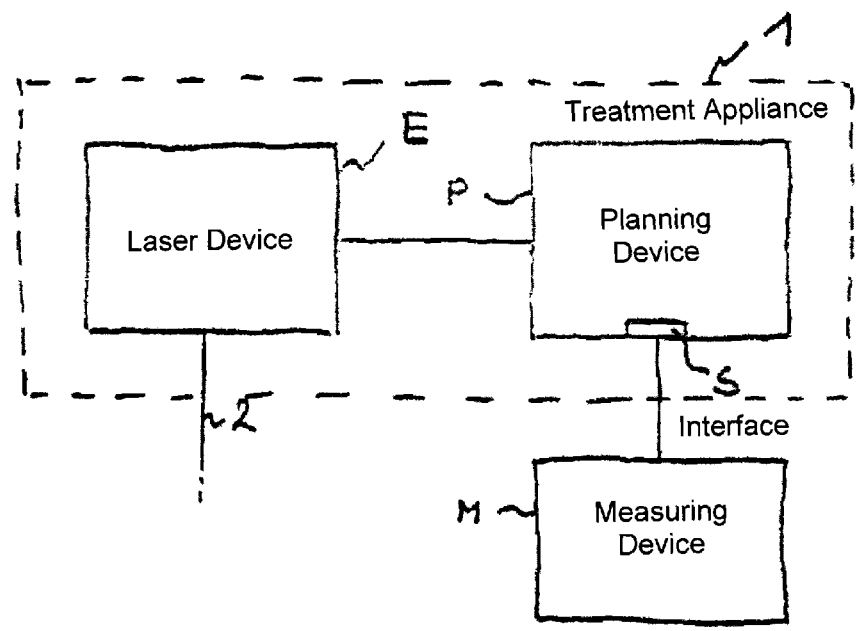
FIG. 1a is a schematic representation in respect of the structure of the treatment appliance of FIG. 1.

The treatment appliance 1 is shown schematically in FIG. 1a. In this variant, it has at least two devices or modules. A laser device E emits the laser beam 2 to the eye 3. The operation of the laser device E in this case is fully automatic, i.e. upon a corresponding start signal, the laser device E starts to deflect the laser beam 2 and thereby produces cut surfaces, which, in a manner to be described, are built up and isolate a volume in the cornea of the eye. The control data necessary for operation is received, as a control data set, previously by the laser device E from a planning device P, via control lines that are not denoted in greater detail. The data is transmitted prior to operation of the laser device E. Clearly, communication can also be effected wirelessly. As an alternative to direct communication, it is also possible to arrange the planning unit P such that it is spatially separate from the laser device E, and to provide a corresponding data transmission channel.

In one embodiment, the control data set is transmitted to the treatment appliance 1 and, further, in some embodiments, operation of the laser device E is blocked until a valid control data set is present at the laser device E. A valid control data set can be a control data set that, in principle, is suitable for use with the laser device E of the treatment apparatus 1. Additionally, however, the validity can also be linked to the passing of further tests, for example whether information, additionally stored in the control data set, concerning the treatment appliance 1, e.g. an appliance serial number, or concerning the patient, e.g. a patient identification number, corresponds to other information that, for example, has been read out or has been input separately at the treatment apparatus as soon as the patient is in the correct position for the operation of the laser device E.

The control data set that is made available to the laser device E for the purpose of performing the operation is generated by the planning unit P from measurement data and defective-vision data that have been established for the eye to be treated. The data is supplied to the planning unit P via an interface S and, in the embodiment example represented, it originates from a measuring device M, which has previously taken measurements of the eye of the patient 4. Clearly, the measuring device M can transfer the corresponding measurement and defective-vision data to the planning device P in any manner.

Figure 2:
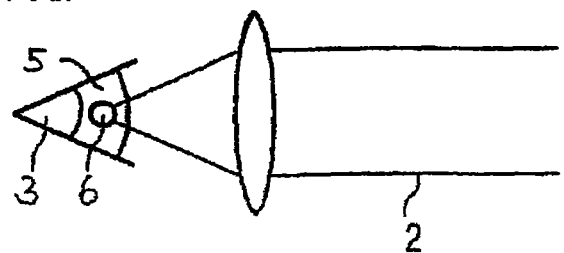
FIG. 2 is an elementary representation concerning the introduction of pulsed laser radiation into the eye in the correction of defective vision by means of the treatment appliance of FIG. 1.

The functioning of the laser beam 2 is indicated schematically in FIG. 2. The treatment laser beam 2 is focused into the cornea 5 of the eye 6 by means of an optical train that is not denoted in greater detail. There is thereby produced in the cornea 5 a focus that covers a spot 6 and in which the energy density of the laser radiation is of such magnitude that, in combination with the pulse length, it produces a non-linear effect in the eye. For example, each pulse of the pulsed laser radiation 2 at the respective spot 6 can produce an optical breakdown in the cornea 5 of the eye, which breakdown, in turn, initiates a plasma bubble, indicated schematically in FIG. 2. As a result, tissue is separated in the cornea 5 by means of this laser pulse. Upon the development of a plasma bubble, the tissue layer separation comprises a larger region than the spot 6 covered by the focus of the laser radiation 2, although the conditions for producing the breakdown are achieved only in the focus. In order for an optical breakdown to be produced by each laser pulse, the energy density, i.e. the fluence, of the laser radiation must be above a certain threshold value, which is dependent on pulse length. Persons skilled in the art know of this relationship from, for example, DE 69500997 T2.

Alternatively, a tissue-separating effect can also be produced by the pulsed laser radiation in that a plurality of laser radiation pulses are emitted into a region, the spots 6 overlapping for a plurality of laser radiation pulses. A plurality of laser radiation pulses then act together to achieve a tissue-separating effect.

However, the nature of the tissue separation used by the treatment appliance 1 is of no further relevance to this description. It is substantive only that the treatment appliance 1 realizes in the tissue a cut surface whose shape is characterized by points in the tissue. These points can specify, for example, target points for a focus location, one or more laser pulse(s) being emitted at the target points. The definition of points in the tissue/material is important for the procedures and apparatuses explained in the following, and is to be described in yet greater detail. This description is based, merely by way of example, on the points being target points for pulsed laser radiation.

In order to perform a correction of defective vision, the pulsed laser radiation is used to remove material from a region within the cornea 5, in that tissue layers are separated therein, which isolate the material and then enable material to be removed. The removal of material causes the volume of the cornea to be altered, resulting in a change in the optical imaging action of the cornea 5, this change being calculated with such precision that the previously ascertained defective vision thereby is corrected insofar as possible. For the purpose of isolating the volume to be removed, the focus of the laser radiation 2 is directed onto target points in the cornea 5, normally in a region located beneath the epithelium and the Bowman's membrane and above the Decemet's membrane and the endothelium. For this purpose, the treatment appliance 1 has a mechanism for adjusting the position of the focus of the laser radiation 2 in the cornea 5. This is shown schematically in FIG. 3.

In FIG. 3, elements of the treatment appliance 1 are shown only to the extent necessary for understanding of the focus adjustment. As already mentioned, the laser radiation 2 is bundled in a focus 7 in the cornea 5, and the position of the focus 7 in the cornea is adjusted such that, for the purpose of producing a cut surface, energy from laser radiation pulses is introduced into the tissue of the cornea 5 in a focused manner at various locations. The laser radiation 2 is provided, as pulsed radiation, by a laser 8. An xy scanner 9, which, in a variant, is realized by two substantially orthogonally deflecting galvanometric mirrors, effects two-dimensional deflection of the laser beam coming from the laser 8, such that, after the xy scanner 9, a deflected laser beam 10 is present. The xy scanner 9 therefore causes the position of the focus 7 to be adjusted substantially perpendicularly to the main direction of incidence of the laser radiation 2 into the cornea 5. In addition to the xy scanner 9, a z scanner 11, which is realized, for example, as an adjustable telescope, is provided for adjusting the depth position. The z scanner 11 is used to alter the z position of the focus 7, i.e. its position on the optical incidence axis. The z scanner 11 can be arranged before or after the xy scanner 9. The coordinates denoted by x, y, z in the following thus relate to the deflection of the position of the focus 7.

The assignment of the individual coordinates to the spatial directions is not determinative for the definition of the points in the cornea 5; in the following, however, to simplify description, the coordinate along the optical incidence axis of the radiation 2 is always denoted by z, and x and y denote two coordinates that are orthogonal to one another in a plane perpendicular to the direction of incidence of the laser beam. Clearly, persons skilled in the art know that the position of the points in the cornea 5 can also be described three-dimensionally by other coordinate systems, in particular that the coordinate system need not be a system of rectangular coordinates. Likewise, it is not absolutely necessary for the xy scanner 9 to deflect axes that are at right angles to one another; rather, it is possible to use any scanner capable of adjusting the focus 7 in a plane in which the incidence axis of the optical radiation does not lie. Oblique-angled coordinate systems are therefore also possible.

Further, non-Cartesian coordinate systems can also be used to describe, or control, the position of the focus 7, as is also to be explained further in the following. Examples of such coordinate systems are ball coordinates (also termed spherical coordinates) and cylinder coordinates.

For the purpose of controlling the position of the focus 7 onto the target points, the xy scanner 9 and the z scanner 11, which together realize an actual example of a three-dimensional focus adjustment device, are controlled by a control device 12, via lines not denoted in greater detail. The same applies to the laser 8. The control device 12 provides for an appropriately synchronous operation of the laser 8 and of the three-dimensional focus adjustment device, realized exemplarily by the xy scanner 9 and the z scanner 11, such that the position of the focus 7 in the cornea 5 is adjusted in such a way that, ultimately, a defined volume of material is isolated, the subsequent removal of volume effecting a desired correction of defective vision.

The control device 12 operates according to specified control data, which specifies the target points for the focus adjustment. The control data is normally combined in a control data set. In one embodiment, this control data set specifies the coordinates of the target points as a pattern, the sequence of the target points in the control data set specifying the serial arrangement of the focus positions and thus, ultimately, a path curve (also referred to here in short as a path). In one embodiment, the control data set contains the target points as actual correcting-variable values for the focus position adjusting mechanism, e.g. for the xy scanner 9 and the z scanner 11. For the purpose of preparing the eye-surgery procedure, i.e. before the actual operation procedure can be performed, the target points, and in some embodiments also their sequence in the pattern, are determined. There must be pre-planning of the operation to determine the control data for the treatment apparatus 1, which, when applied, then achieves for the patient 4 an optimal correction of defective vision.

The control data ultimately causes cut surfaces to be produced, in that the target points are specified in an appropriate manner in the cornea. It is described in the prior art, for example in WO 2005/011546, for the purpose of producing cut surfaces in the cornea of the eye, that special spirals can be used, which spirals run, for example, in the manner of a helix, around a main axis that is substantially perpendicular to the optical axis (z axis). The use of a scan pattern, which arranges the target points in rows, is also known (cf. WO 2005/011545). Clearly, these possibilities can be used to produce the cut surfaces defined above and can be used with the transformations explained in the following.

The adjustment of the position of the focus in the cornea of the eye is effected by means of the three-dimensional deflection device, represented schematically in FIG. 3, which, for the purpose of adjusting the focus in the z direction, employs the displacement of lenses or of other optically acting elements.

Figure 4:
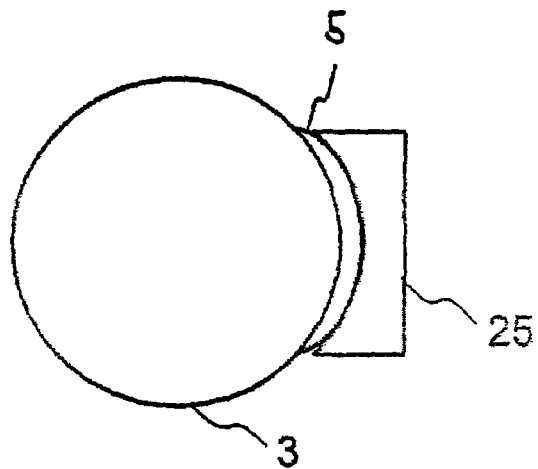
FIG. 4 is a schematic representation to explain the function of a contact glass in the treatment appliance of FIG. 1, FIGS. 5 to 7 are schematic representations in respect of the effects of the contact glass resulting from deformation of the cornea of the eye, [[and]]

In the determination of the target points it must, of course, be taken into consideration, particularly in the case of correction of defective vision, that a volume to be removed is ultimately to be defined with the eye in the normal state. The cut surfaces ultimately of interest therefore relate to the natural eye. However, it must then be taken into consideration that, for reasons of fixing the eye in place, the treatment appliance 1 operates with a contact glass 25, which, as shown in FIG. 4, is placed onto the anterior surface 15 of the cornea 5 of the eye. In respect of this present description of the treatment appliance 1, or of the therewith associated procedures for preparing and/or performing the surgical operation, however, the contact glass 25, which already constitutes subject-matter of a plurality of patent publications (reference is made exemplarily to, for example, WO 2005/048895), is of interest only to the extent that it imparts a defined curvature to the corneal anterior surface 15. In respect of the spherical curvature of the contact surface of the contact glass 25, however, the approach described here differs markedly from the approach as described, for example, in WO 2003/002008, which uses a planar contact glass that presses the cornea of the eye flat.

Figure 5:
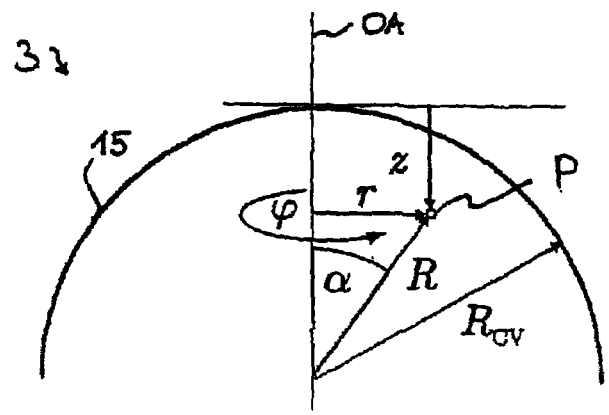
Figure 6:
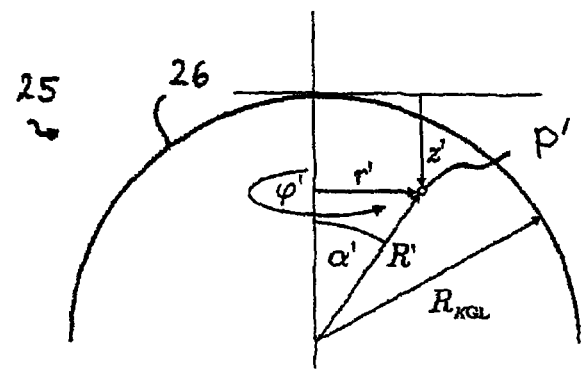
Figure 7:
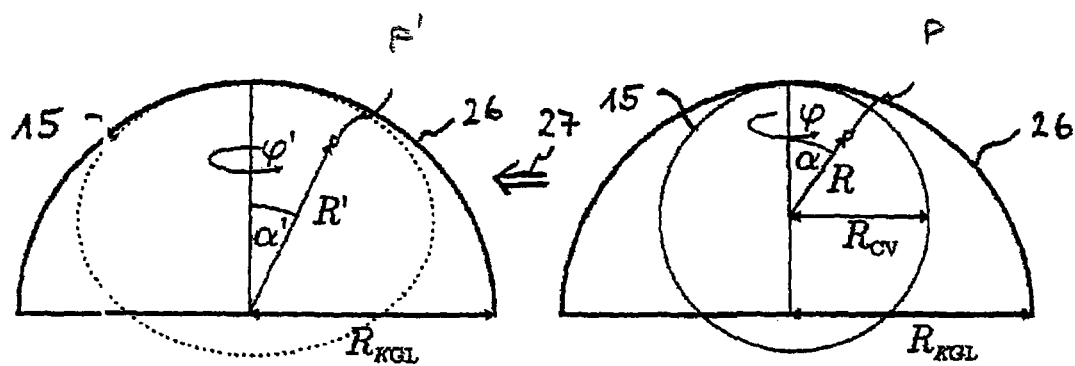

When the eye is pressed onto the contact glass 25 having a spherical contact surface, a spatial deformation of the eye occurs. The pressing-on corresponds to a transformation of the coordinate system of the eye, as represented exemplarily in FIG. 5, into the coordinate system of the contact glass, which is shown by way of example in FIG. 6. Persons skilled in the art know of this relationship from WO 2005/011547, the disclosed content of which is to be included to its full extent in this regard. In FIGS. 5 and 6, coordinates marked with an apostrophe denote the coordinates of the quantities related to the contact glass 25, or to its contact-glass underside 26 that faces towards the eye. A given point P in the free cornea (FIG. 5) then corresponds to a point P' in the cornea when pressed on to the contact surface 25 (FIG. 7, left).

The contact glass, however, has yet a further advantage. By being pressed on to the contact-glass underside 26, the corneal anterior surface 15 is also automatically spherical. A surface located at a constant distance under the corneal anterior surface 15 is therefore likewise spherical when the contact glass has been pressed on, such that control is simplified considerably. For this reason, it has always been attempted hitherto to use a contact glass 25 having a spherical contact-glass underside 26 and to specify, at least for one cut surface, target points that define this cut surface as a spherical surface at a constant distance under the corneal anterior surface 15.

The representations in FIGS. 5 and 6 show the coordinate transformation that occurs on the eye as a result of the contact glass being placed on or removed. They include both spherical coordinates (R, α, φ) related to the origin of the curved surface (corneal anterior surface 15, or contact-glass underside 26) and cylinder coordinates (R, z, φ) related to the vertex of the corneal anterior surface 15, or of the contact-glass underside 26, the vertex being defined by the through-passage point of the optical axis OA.

A coordinate transformation occurs quite independently of the selected coordinate systems, however, if a point in the cornea in the free (or pressed-on) eye has been given and is to be described in the pressed-on (or free) eye.

In the case of the coordinate transformation from the coordinate system related to the free eye, as represented in FIG. 7, to the system of the pressed-on eye related to the contact glass, according to FIG. 7, the arc length, i.e. α·R, the radial depth ($R_{CV}$–R) and the angle φ are maintained. The transformation of target points taken as a basis for the natural eye, i.e. in the coordinate system of FIG. 7, is thus an important step in the calculation of the control quantities for the three-dimensional focus adjustment device. Its realization differs fundamentally from that in the case of a flat contact glass, in which, for example, a spherical surface degenerates into a plane.

The pressing of the cornea 5 of the eye 3 onto the spherically curved contact-glass underside 26 is illustrated in FIG. 7. There, the representation on the right shows, schematically, the state when the contact-glass underside 26 is in contact with the corneal anterior surface 15 only at the vertex. The cornea is still non-deformed. For the purpose of elucidating the geometric relationships, the corneal anterior surface 15 is represented schematically as a circle in FIG. 7. The pressing of the contact glass 25 onto the cornea 5 effects the transition to the state on the left side of FIG. 7, which transition is represented by the arrow 27. The removal of the contact glass 25 effects a relaxation of the eye 3 contrary to the direction of the arrow 27.

Owing to the boundary conditions described, for each point in the cornea 5 of the eye the coordinates are transformed from the system represented in FIG. 5 to the system of FIG. 6. Since the placing-on of the corneal anterior surface 15 is normally effected by suction, by means of negative pressure, the transformation is referred to in the following as a suction transformation.

The following procedure provides for a general transformation of the coordinates of a point P of the relaxed eye (not subjected to suction) into coordinates for a corresponding point P' of the eye subjected to suction. The back transformation is then described. This general approach does not require any special geometry of the contact glass or of the corneal anterior surface, but it uses a corneal anterior surface that is the anterior surface of the cornea without a tear film:

1. Numerical or analytical description of the anterior surface 15 of the cornea in any coordinate system, with experimental determination and, if necessary, use of appropriate smoothing methods. In the case of consideration of a position of the bend line (or neutral axis) at a distance L under the anterior surface 15 of the cornea, in the case of the suction transformation a reference surface V, which is contracted radially by L in relation to the anterior surface 15, is used instead of the anterior surface 15. If the bend line is not to be taken into consideration, the reference surface V is the same as the anterior surface 15 of the cornea 5.

2. Numerical or analytical description of the contact surface 26 of the contact glass 25 in any coordinate system, with experimental determination and, if necessary, use of appropriate smoothing methods. In the transformation, the contact surface 26 is considered to be that surface assumed by the anterior surface 15 of the cornea 5 in the pressed-on eye. In the case of consideration of a fluid film thickness F' and/or bend line displacement L, however, a contact-glass reference surface G, which is contracted radially by F'+L in relation to the contact surface 26, is to be used instead of the contact surface 26. If a fluid film thickness F' and a bend line displacement L are not to be taken into consideration, then, in this case likewise, the contact surface 26 and the contact-glass reference surface G coincide.

3. Determination of the point of origin A of the transformation, which point of origin is located in the reference surface V and which does not change its coordinates during the transformation. This point can be the point of intersection of the optic axis and the reference surface V or of the geometric vertex of the reference surface V. Here, both points are combined under the term "vertex".

4. Determination of the point M on the contact-glass reference surface G that is least distant from the point of origin A after suction. As a good approximation, A=M.

5. Determination of all points $O_i$ (φ) on the reference surface V on whose surface normals the point P (φ) is located. The surface normal in this case is to be understood as a straight line that is perpendicular to the reference surface V and contains the points $O_i$.

6. Determination of the O∈$O_i$ for which the segment $\overline{PO_i}$ is a minimum. This is thus the point of intersection between the surface normals and the reference surface V.

7. Calculation of the curve length $$B_\varphi = \int_{O(\varphi)}^{A} V$$

from O to A in the plane of intersection characterized by the cylinder angle φ.

8. Calculation of the point O'∈G for which the following is applicable:

$$B_\varphi = \int_{O'(\varphi)}^{M} G.$$

9. Calculation of the point P'(φ) for which the following is applicable: $\overline{P'O'}$ and $\overline{PO}$ 10. The following always applies: φ'=φ.

The back transformation is performed using the following steps:

1. Numerical or analytical descriptions in a manner analogous to Points 1 and 2 above.

2. The procedure stated under No. 3 above is used for the point of origin.

3. Determination of the point M on the contact-glass reference surface G that is least distant from the point of origin A of the transformation. As a good approximation, A=M.

4. Determination of all points $O_i$' (φ) on the contact-glass reference surface G on whose surface normals the point P' (φ) is located. The surface normal is again the straight line that is perpendicular to the contact-glass reference surface G and contains the point $O_i$'.

5. Determination of the point O'∈$O_i$' for which the segment $\overline{P'O'_i}$ is a minimum.

6. Calculation of the curve length $$B'_\varphi = \int_{O'(\varphi)}^{A'} G$$

from O' to A' in the plane of intersection characterized by the cylinder angle φ.

7. Calculation of the O∈V for which the following is applicable:

$$B'_\varphi = \int_{O'(\varphi)}^M V.$$

8. Calculation of the point P(φ) for which the following is applicable: $\overline{P'O'}$ and $\overline{PO}$.

9. The following always applies: φ'=φ.

The above method can be used to perform the suction transformation for any surface forms, both of the corneal anterior surface 15 and of the contact-glass contact surface 26.

If the points to be transformed are at a distance from the respective reference surface that is less than the local radius of curvature of the reference surface, the points No. 5 of the forward transformation and No. 4 of the back transformation can be omitted. The local radius of curvature is obtained from the radius of a best-matched sphere at the corresponding point, and can be approximated, in a simplified manner, with the least radius of curvature of the surface. In the case of eye surgery, the conditions for omission of the points No. 5 or No. 4 are usually fulfilled, since the cornea is significantly thinner than its radius of curvature.

There is a special solution for the special condition of a paraboloidal surface of the corneal anterior surface and a spherical contact glass shape, which thus shows parabolas in the radial split image. A parabola still corresponds somewhat better to the natural shape of the eye 5 than does the solution, already known in the prior art, for any given sphere.

A simplification of this special solution that is particularly saving in computation is provided by the following expansion of the suction transformations, known from WO 2005/011547, for a spherical corneal anterior surface on a spherical contact glass to a paraboloid-shaped corneal anterior surface:

$$\varphi = \varphi'$$

$$\alpha' \cdot (R' - F' - L) = (R - L) \cdot \left(\alpha + \frac{c_5}{40}\alpha^5 - \frac{c_7}{84}\alpha^7 + K_1\right)$$

$$R' = R_{KGL} + R - R_{cv}\left(1 + \frac{f_4}{8}\alpha^4 - \frac{f_6}{12}\alpha^6 + K_2\right)$$

The known spherical approach is thus modified, in order to take account of deviations from the ideally spherical shape of the anterior surface 15 of the cornea 5 (or of the contact glass 25) towards a parabola.

Occasionally, the analytically deduced prefactors have to undergo further adaptation on the basis of experimental data. Experimentally determined values other than 1 can thus be assigned to the prefactors $c_i$, $f_i$, in order to take account of deviations of the corneal anterior surface 15 from a paraboloid in the direction of a sphere or an ellipsoid.

If the fluid film thickness F', in the pressed-on state, and a bend line displaced inwards from the anterior surface 15 of the cornea 5 by a distance L are to be taken into consideration, the suction transformation for a spherical contact glass and a spherical corneal anterior surface can be written in the following form.

φ=φ'

$\alpha' \cdot (R_{KGL} - F' - L) = \alpha \cdot (R_{CV} - L)$ $R_{KGL} - R' = R_{CV} - R$ Many measuring devices measure the radius of curvature of the corneal anterior surface 15 inclusive of a thickness T of the natural tear film, and thus directly provide the value $R_{CV}$+T, which must be corrected accordingly, since the above equations are based on $R_{CV}$. It is to be noted that, clearly, this approach can be combined with the transformations described. Also, T, F and/or L can be disregarded for simplification.

Figure 8:
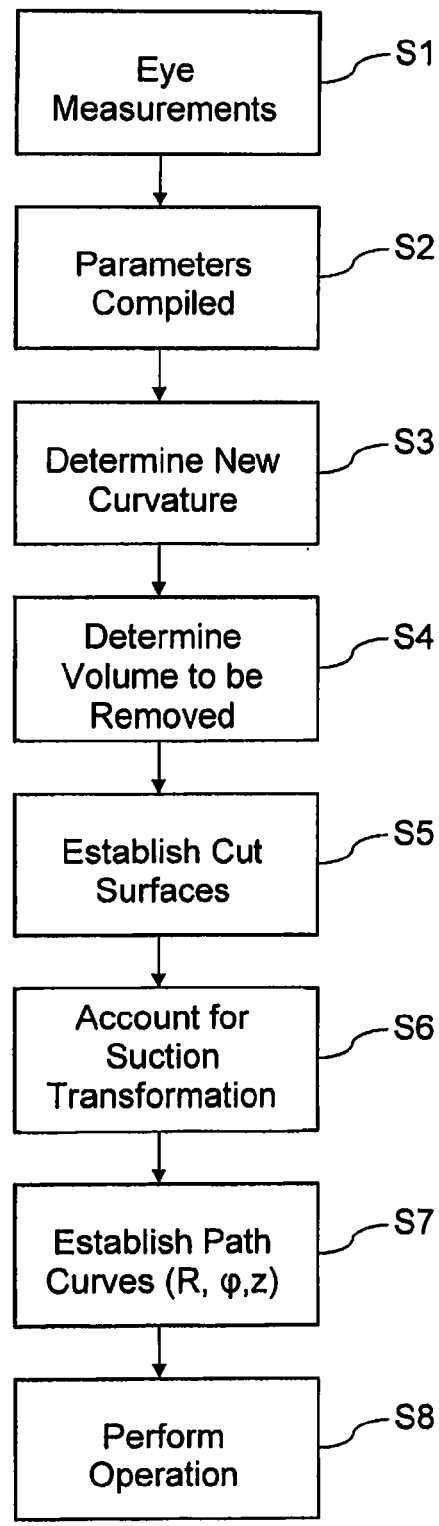
FIG. 8 is a schematic representation of the process in the preparation and execution of a correction of defective vision
Figure 9:
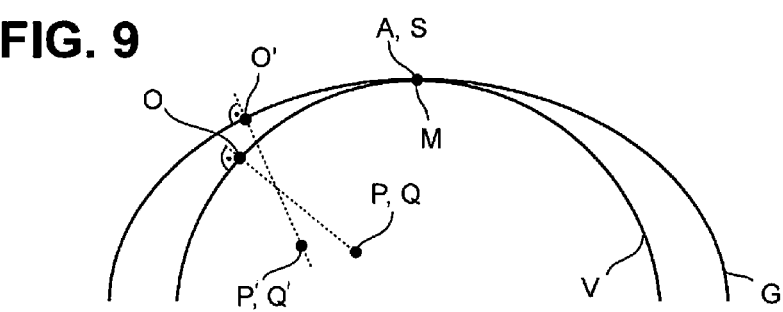
FIG. 9 is a schematic depiction of the cornea in a deformed and undeformed state.
Figure 10:
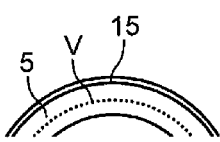
FIG. 10 is a schematic depiction of the cornea in an undeformed state.
Figure 11:
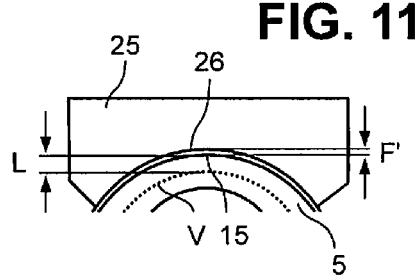
FIG. 11 is a schematic depiction of a contact glass and the cornea in a deformed state.

The sequence of the preparation of the device 1 for application in the case of an eye-surgery operation for defective vision is summarized schematically in FIG. 8. In a step S1, measurements of the eye 3 are taken. In this step, correction parameters are obtained for the defective vision of the patient 4. The parameters compiled in step S2 are then used, in a step S3, to determine the new curvature of the cornea 5 that is necessary for correction. When this calculation in step S3 has been completed, the volume that must be removed from the cornea in order to alter the curvature is determined in S4. For this purpose, in a step S5, cut surfaces that bound the volume are established. Once the corresponding functional descriptions of these surfaces have been obtained, the suction transformation that results when the eye is drawn onto the contact glass by suction is taken into account in step S6. One of the relationships described above is used in this case.

Next is the establishment of the coordinates of the path curves from which the cut surfaces are composed. This is indicated schematically in step S7 by the parameters R, φ, z. At the end of step S7, a point pattern is obtained, which has the coordinates of the spots to which a laser radiation pulse is to be applied in each case. At this stage, already, the density of the target points can be reduced in order to simplify the amount of computation.

With the thus established control parameters, the actual operation is then performed in step S8, and the volume to be removed is bounded by the cut surfaces.

The invention claimed is:

1. A computer implemented method of generating control data for an eye-surgery treatment apparatus that, by application of a laser device, separates tissue layers in a cornea of an eye, wherein, during operation of the laser device, a contact glass having a contact surface is pressed against the cornea and deforms the cornea to conform to a shape of the contact surface, the method comprising:
generating the control data for the laser device such that the control data specifies target point coordinates for the laser device that are located in the cornea and,
taking into account, in the generation of the target-point coordinates, the deformation of the cornea, caused by the contact glass, that exists during the operation of the laser device,
wherein the taking into account the deformation of the cornea comprises execution of the following to determine a displacement of a point P in the non-deformed cornea, the displacement being caused by deformation:
determining, on a reference surface of the non-deformed cornea, in relation to the point P, a point O that is located such that a surface normal running through the point O goes through the point P, the reference surface being either the anterior surface of the cornea or a surface obtained through radial contraction of the anterior surface by a bend line displacement L,
determining a distance $\overline{SO}$ between a vertex S of the reference surface and the point O, the distance $\overline{SO}$ being the arc length on the reference surface,
determining on a contact-glass reference surface a point O' that is located at the distance $\overline{SO}$ from a contact-surface vertex, the contact-glass reference surface being either the contact surface of the contact glass or a surface obtained through radial contraction of the contact surface by the bend line displacement L and/or by a thickness F' of a fluid film on the cornea, determining, on a surface normal through the point O', a point P' that has the same distance from O' as the point P has from the point O, and using the point P' as a point P displaced by the deformation;

and/or wherein the taking into account the deformation of the cornea comprises execution of the following to determine a displacement of a point Q' in the deformed cornea, the displacement being caused by relaxation:

determining on the contact-glass reference surface, in relation to the point Q', a point O' that is located such that a surface normal running through the point O' goes through the point Q', determining a distance $\overline{SO'}$ between the vertex S and the point O', the distance $\overline{SO'}$ being the arc length on the contact-glass reference surface, determining, on the reference surface, a point O that is located at the distance $\overline{SO'}$ from the vertex S, determining, on a surface normal through the point O, a point Q that has the same distance from O as the point Q' has from the point O', and using the point Q as a point Q' displaced by the relaxation.

2. A computer implemented method of generating control data for an eye-surgery treatment apparatus that, by application of a laser device, separates tissue layers in a cornea of an eye, wherein, during operation of the laser device, a contact glass having a contact surface is pressed against the cornea and deforms the cornea to conform to the shape of the contact surface, the method comprising:

generating the control data for the laser device such that the control data specifies target point coordinates for the laser device that are located in the cornea and, taking into account, in the generation of the target-point coordinates, the deformation of the cornea, caused by the contact glass, that exists during the operation of the laser device, wherein the taking into account the deformation of the cornea comprises using the following transformation, between a spherical coordinate system ($\phi$, $\alpha$, R), related to the non-deformed cornea, and a spherical coordinate system ($\phi'$, $\alpha'$, R') for the cornea placed against the contact glass and deformed thereby:

$$\varphi = \varphi'$$

$$\alpha' \cdot R' = R \cdot \left(\alpha + \frac{c_5}{40}\alpha^5 - \frac{c_7}{84}\alpha^7 + K_1\right)$$

$$R' = R_{KGL} + R - R_{cv}\left(1 + \frac{f_4}{8}\alpha^4 - \frac{f_6}{12}\alpha^6 + K_2\right)$$

wherein $R_{KGL}$ is a radius of the contact surface, $R_{CV}$ is a radius of the non-deformed anterior surface of the cornea, $c_5$, $c_7$, $f_4$ and $f_6$ are experimentally established correction factors that can be equated approximately to 1, $K_1$ is a first optional correction term for higher odd orders of $\alpha$, and $K_2$ is a second an optional correction term for higher odd orders of $\alpha$.

3. A computer implemented method of generating control data for an eye-surgery treatment apparatus that, by application of a laser device, separates tissue layers in the cornea of the eye, wherein, during operation of the laser device, a contact glass having a contact surface is pressed against the cornea and deforms the cornea to conform to the shape of the contact surface, the method comprising:

generating the control data for the laser device such that the control data specifies target point coordinates for the laser device that are located in the cornea; and, taking into account, in the generation of the target-point coordinates, the deformation of the cornea, caused by the contact glass, that exists during operation of the laser device;

wherein the taking into account the deformation of the cornea comprises using the following transformation, between a spherical coordinate system ($\phi$, $\alpha$, R), related to the non-deformed cornea, and a spherical coordinate system ($\phi'$, $\alpha'$, R') for the cornea that is placed against the contact glass and deformed:

$$\phi = \phi'$$

$$\alpha'(R_{KGL} - F' - L) = \alpha(R_{CV} - L)$$

$$R' = R + R_{KGL} - R_{CV}$$

wherein $R_{KGL}$ is a radius of the contact surface, $R_{CV}$ is a radius of the non-deformed anterior surface of the cornea, F' is a thickness of a fluid film between the cornea and the contact surface pressed against it, and L is a displacement of a bend line of the cornea of the eye from the surface of the cornea into the interior of the cornea, the displacement having been determined experimentally, F' or L being equated approximately to zero.

4. An eye-surgery treatment apparatus that executes the method according to claim 1, comprising:

a laser device for separating tissue layers of the cornea of the eye, a contact glass, having a contact surface and which, during operation of the laser device, deforms the cornea to conform to the shape of the contact surface, wherein the contact surface is first set, with a contact-surface vertex, onto a corneal vertex and then is pressed against the cornea to deform the cornea, a control device, that generates control data for the laser device such that the control data specifies of target point coordinates for the laser device that are located in the cornea, and which, in the generation of the target-point coordinates, considers the deformation of the cornea, caused by the contact glass that exists during the operation of the laser device, wherein the control device executes the method according to claim 1.

5. An eye-surgery treatment apparatus that executes the method according to claim 2, comprising:

a laser device for separating tissue layers of the cornea of the eye, a contact glass, having a contact surface and which, during operation of the laser device, deforms the cornea to conform to the shape of the contact surface, wherein the contact surface is first set, with a contact-surface vertex, onto a corneal vertex and then is pressed against the cornea to deform the cornea, a control device, that generates control data for the laser device such that the control data specifies of target point coordinates for the laser device that are located in the cornea, and which, in the generation of the target-point coordinates, considers the deformation of the cornea, caused by the contact glass that exists during the operation of the laser device, wherein the control device executes the method according to claim 2.

6. An eye-surgery treatment apparatus that executes the method according to claim 3, comprising:
- a laser device for separating tissue layers of the cornea of the eye,
- a contact glass, having a contact surface and which, during operation of the laser device, deforms the cornea to conform to the shape of the contact surface, wherein the contact surface is first set, with a contact-surface vertex, onto a corneal vertex and then is pressed against the cornea to deform the cornea,
- a control device, that generates control data for the laser device such that the control data specifies of target point coordinates for the laser device that are located in the cornea, and which, in the generation of the target-point coordinates, considers the deformation of the cornea, caused by the contact glass that exists during the operation of the laser device,
- wherein the control device executes the method according to claim 3.

7. A method of eye-surgery treatment that, by application of a laser device, separates tissue layers in the cornea of an eye, comprising:
- pressing a contact glass having a contact surface against the cornea, such that the contact glass deforms the cornea to conform to a shape of the contact surface;
- generating control data for the laser device such that the control data specifies target point coordinates for the laser device that are located in the cornea and,
- taking into account, in the generation of the target-point coordinates, the deformation of the cornea, caused by the contact glass, that exists during the operation of the laser device;
- wherein the taking into account the deformation of the cornea comprises execution of the following to determine a displacement of a point P in the non-deformed cornea, the displacement being caused by deformation:
  - determining on a reference surface of the non-deformed cornea, in relation to the point P, a point O that is located such that the surface normal running through the point O goes through the point P, the reference surface being either the anterior surface or a surface obtained through radial contraction of the anterior surface by a bend line displacement L,
  - determining a distance $\overline{SO}$ between a vertex S of the reference surface and the point O is determined, the distance $\overline{SO}$ being the arc length on the reference surface,
  - determining on a contact-glass reference surface a point O' that is located at the distance $\overline{SO}$ from the contact-surface vertex, the contact-glass reference surface being either the contact surface or a surface obtained through radial contraction of the contact surface by the bend line displacement L and/or by a thickness F' of a fluid film on the cornea,
  - determining, on a surface normal through the point O' a point P' that has the same distance from O' as the point P has from the point O, and
  - using the point P' as a point P displaced by the deformation;
- and/or wherein the taking into account the deformation of the cornea comprises execution of the following to determine a displacement of a point Q' in the deformed cornea, the displacement being caused by relaxation:
  - determining, on the contact-glass reference surface, in relation to the point Q', a point O' that is located such that the surface normal running through the point O' goes through the point Q',
  - determining a distance $\overline{SO'}$ between the vertex S and the point O', the distance $\overline{SO'}$ being the arc length on the contact-glass reference surface,
  - determining on the reference surface a point O that is located at the distance $\overline{SO'}$ from the vertex S,
  - determining on a surface normal in the point O a point Q that has the same distance from O as the point Q' has from the point O', and
  - using the point Q as a point Q' displaced by the relaxation.

8. A method of eye-surgery treatment that, by application of a laser device, separates tissue layers in the cornea of the eye, comprising:
- pressing a contact glass having a contact surface against the cornea, such that the contact glass deforms the cornea to conform to the shape of the contact surface;
- generating control data for the laser device such that the control data specifies target point coordinates for the laser device that are located in the cornea and,
- taking into account, in the generation of the target-point coordinates, the deformation of the cornea, caused by the contact glass, that exists during the operation of the laser device;
- wherein the taking into account the deformation of the cornea comprises using the following transformation, between a spherical coordinate system ($\phi$, $\alpha$, R), related to the non-deformed cornea, and a spherical coordinate system ($\phi'$, $\alpha'$, R') for the cornea that is placed against the contact surface and deformed:

$$\varphi = \varphi'$$
$$\alpha' \cdot R' = R \cdot \left(\alpha + \frac{c_5}{40}\alpha^5 - \frac{c_7}{84}\alpha^7 + K_1\right)$$
$$R' = R_{KGL} + R - R_{Cv}\left(1 + \frac{f_4}{8}\alpha^4 - \frac{f_6}{12}\alpha^6 + K_2\right)$$

wherein $R_{KGL}$ is the radius of the contact surface, $R_{CV}$ is the radius of the non-deformed anterior surface of the cornea, $c_5$, $c_7$, $f_4$ and $f_6$ are experimentally established correction factors that can be equated approximately to 1, $K_1$ is a first optional correction term for higher odd orders of $\alpha$, and $K_2$ is a second optional correction term for higher odd orders of $\alpha$.

9. The method according to claim 2, comprising reducing the radius R' by (F'+L) in the second equation and reducing the radius R by L for the purpose of taking into consideration a thickness F' of a fluid film on the cornea and/or a bend line displacement L.

10. The method according to claim 8, comprising reducing the radius R' by (F'+L) in the second equation and reducing the radius R by L for the purpose of taking into consideration a thickness F' of a fluid film on the cornea and/or a bend line displacement L.

11. A method of eye-surgery treatment that by application of a laser device, separates tissue layers in the cornea of the eye, comprising:
- pressing a contact glass having a contact surface against the cornea, such that the contact glass deforms the cornea to conform to the shape of the contact surface;
- generating control data for the laser device such that the control data specifies target point coordinates for the laser device that are located in the cornea; and
- taking into account, in the generation of the target-point coordinates, the deformation of the cornea, caused by the contact glass, that exists during the operation of the laser device;

wherein the taking into account the deformation of the cornea comprises using the following transformation, between a spherical coordinate system ($\phi$, $\alpha$, R), related to the non-deformed cornea, and a spherical coordinate system ($\phi'$, $\alpha'$, R') for the cornea that is placed against the contact surface and deformed:

$\phi = \phi'$ $\alpha'(R_{KGL} - F' - L) = \alpha(R_{CV} - L)$ $R' = R + R_{KGL} - R_{CV}$ wherein $R_{KGL}$ is a radius of the contact surface, $R_{CV}$ is a radius of the non-deformed anterior surface of the cornea, F' is a thickness of a fluid film between the cornea and the contact surface pressed against it, and L is a displacement of a bend line of the cornea of the eye from the surface of the cornea into the interior of the cornea, which displacement has been determined experimentally, F' or L being equated approximately to zero.

* * * * *

UNITED STATES PATENT AND TRADEMARK OFFICE
CERTIFICATE OF CORRECTION

PATENT NO. : 8,632,527 B2
APPLICATION NO. : 12/936380
DATED : January 21, 2014
INVENTOR(S) : Mark Bischoff et al.

It is certified that error appears in the above-identified patent and that said Letters Patent is hereby corrected as shown below:

In the Specification

Col. 4, line 47, delete "ф" and insert --φ--

Col. 4, line 48, delete "ф'" and insert --φ'--

Col. 5, line 12, delete "ф" and insert --φ--

Col. 5, line 13, delete "ф'" and insert --φ'--

Col. 5, line 16, delete "ф=ф'" and insert --φ=φ'--

Col. 6, line 15, after "the", insert --point--

Col. 6, line 34, delete "ф" and insert --φ--

Col. 6, line 35, delete "ф'" and insert --φ'--

Col. 6, line 65, delete "ф" and insert --φ--

Col. 6, line 66, delete "ф'" and insert --φ'--

Col. 7, line 1, delete "ф=ф'" and insert --φ=φ'--

Col. 8, line 51, delete "[[and]]"

Col. 12, line 60, delete "ф" and insert --φ--

Col. 12, line 62, delete "ф" and insert --φ--

Col. 14, line 11, delete "ф" and insert --φ--

Col. 14, line 12, delete "ф" and insert --φ--

Col. 14, line 27, delete "ф" and insert --φ--

Signed and Sealed this
Nineteenth Day of August, 2014

Michelle K. Lee
*Deputy Director of the United States Patent and Trademark Office*

Col. 14, line 39, delete "ϕ'-ϕ" and insert --φ'=φ--

Col. 14, line 49, delete "ϕ" and insert --φ--

Col. 14, line 50, delete "ϕ" and insert --φ--

Col. 14, line 65, delete "ϕ" and insert --φ--

Col. 15, line 8, delete "ϕ'=ϕ" and insert --φ'=φ--

Col. 15, line 60, delete "ϕ=ϕ'" and insert --φ=φ'--

Col. 16, line 25, delete "ϕ" and insert --φ--

In the Claims

Col. 18, line 12, Claim 3, delete "ϕ" and insert --φ--

Col. 18, line 14, Claim 3, delete "ϕ'" and insert --φ'--

Col. 18, line 16, Claim 3, delete "ϕ=ϕ'" and insert --φ=φ'--

Col. 20, line 26, Claim 3, delete "ϕ" and insert --φ--

Col. 20, line 28, Claim 8, delete "ϕ'" and insert --φ'--

Col. 21, line 3, Claim 11, delete "ϕ" and insert --φ--

Col. 21, line 5, Claim 11, delete "ϕ'" and insert --φ'--

Col. 21, line 7, Claim 11, delete "ϕ=ϕ'" and insert --φ=φ'--

UNITED STATES PATENT AND TRADEMARK OFFICE
CERTIFICATE OF CORRECTION

PATENT NO. : 8,632,527 B2  Page 1 of 1
APPLICATION NO. : 12/936380
DATED : January 21, 2014
INVENTOR(S) : Mark Bischoff et al.

It is certified that error appears in the above-identified patent and that said Letters Patent is hereby corrected as shown below:

In the Specification

Col. 13, line 7, delete "ϕ" and insert --φ--

Col. 15, line 6, delete "ϕ" and insert --φ--

Col. 17, line 46, delete "ϕ" and insert --φ'--

Signed and Sealed this
Twenty-fifth Day of August, 2015

Michelle K. Lee
*Director of the United States Patent and Trademark Office*